United States Patent
Ichiki

(10) Patent No.: US 10,229,480 B2
(45) Date of Patent: Mar. 12, 2019

(54) IMAGE PROCESSING DEVICE, IMAGE PROCESSING METHOD, PROGRAM, AND ENDOSCOPE SYSTEM

(71) Applicant: SONY CORPORATION, Tokyo (JP)

(72) Inventor: Hiroshi Ichiki, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 58 days.

(21) Appl. No.: 15/312,798

(22) PCT Filed: May 29, 2015

(86) PCT No.: PCT/JP2015/065535
§ 371 (c)(1),
(2) Date: Nov. 21, 2016

(87) PCT Pub. No.: WO2015/190319
PCT Pub. Date: Dec. 17, 2015

(65) Prior Publication Data
US 2017/0206640 A1     Jul. 20, 2017

(30) Foreign Application Priority Data
Jun. 11, 2014   (JP) .................... 2014-120206

(51) Int. Cl.
*G06T 5/00* (2006.01)
*A61B 1/04* (2006.01)
(Continued)

(52) U.S. Cl.
CPC .......... *G06T 5/003* (2013.01); *A61B 1/00009* (2013.01); *A61B 1/00135* (2013.01);
(Continued)

(58) Field of Classification Search
CPC ......... G06T 5/003; G06T 7/0012; G06T 7/20; G06T 7/246; G06T 7/248; G06T 7/73;
(Continued)

(56) References Cited

U.S. PATENT DOCUMENTS

2006/0074307 A1 * 4/2006 Igarashi et al. ............... 600/434

FOREIGN PATENT DOCUMENTS

| JP | 05-049599 A | 3/1993 |
| JP | 11-168717 A | 6/1999 |

(Continued)

*Primary Examiner* — Andrew W Johns
(74) *Attorney, Agent, or Firm* — Oblon, McClelland, Maier & Neustadt, L.L.P.

(57) ABSTRACT

The present disclosure relates to an image processing device, an image processing method, a program, and an endoscope system capable of arranging an endoscope so that the endoscope is not fixed to a retractor and has a degree of freedom, and capable of correcting an image deterioration such as a blur that might occur in this case. The image processing device according to an aspect of the present disclosure is the image processing device configured to correct, frame by frame, a motion image having a predetermined frame rate, and the image processing device includes: a marker detecting unit configured to detect a marker provided on an operation tool and photographed in a current frame; a calculation unit configured to calculate a blur correction amount on the basis of a position of the detected marker; and a blur correction unit configured to perform a blur correction on the current frame in accordance with the blur correction amount. The present disclosure can be applied to the endoscope system.

11 Claims, 13 Drawing Sheets

(51) Int. Cl.
　　　*G02B 23/24*　　　(2006.01)
　　　*G03B 5/00*　　　(2006.01)
　　　*H04N 5/232*　　　(2006.01)
　　　*G06T 7/73*　　　(2017.01)
　　　*G06T 7/246*　　　(2017.01)
　　　*A61B 1/00*　　　(2006.01)
　　　*A61B 5/06*　　　(2006.01)

(52) U.S. Cl.
　　　CPC ............ *A61B 1/00154* (2013.01); *A61B 1/04* (2013.01); *A61B 5/061* (2013.01); *A61B 5/064* (2013.01); *G02B 23/24* (2013.01); *G03B 5/00* (2013.01); *G06T 7/248* (2017.01); *G06T 7/74* (2017.01); *H04N 5/232* (2013.01); *G06T 2207/10016* (2013.01); *G06T 2207/10068* (2013.01); *G06T 2207/30196* (2013.01); *G06T 2207/30204* (2013.01)

(58) Field of Classification Search
　　　CPC ............ G06T 7/74; G06T 2207/20201; A61B 1/00009; A61B 5/7207
　　　See application file for complete search history.

(56)　　　　　　　References Cited

FOREIGN PATENT DOCUMENTS

| JP | 2005-323681 A | 11/2005 |
| JP | 2011-502550 A | 1/2011 |
| JP | 2012-239644 A | 12/2012 |

\* cited by examiner

IMAGE PROCESSING DEVICE, IMAGE PROCESSING METHOD, PROGRAM, AND ENDOSCOPE SYSTEM

CROSS REFERENCE TO RELATED APPLICATIONS

This application is a U.S. National Phase of International Patent Application No. PCT/JP2015/065535 filed on May 29, 2015, which claims priority benefit of Japanese Patent Application No. JP 2014-120206 filed in the Japan Patent Office on Jun. 11, 2014. Each of the above-referenced applications is hereby incorporated herein by reference in its entirety.

TECHNICAL FIELD

The present disclosure relates to an image processing device, an image processing method, a program, and an endoscope system. In particular, the present disclosure relates to the image processing device, the image processing method, the program, and the endoscope system suitable for use in, for example, an operation that is performed while an affected area (operation site) is observed by means of an endoscope or an operation microscope.

BACKGROUND ART

Examples of a disease for which an operation is performed on a spine include hernia, osteoporosis, and osteoarthritis. Conventionally, an operation method that exhibits a very low invasiveness with the use of a thin needle is employed for hernia and minimal osteoporosis. An operation method for making a large incision in a patient's back is employed for severe osteoporosis and osteoarthritis (for example, refer to Patent Document 1).

In recent years, an operation method for making an incision only in a required minimum part has been widely used even for a disease that conventionally requires a large incision. In this operation method, an operation is performed in such a manner that a cylindrical retractor (also generally referred to as a sleeve) made of metal is inserted into a small incision part, and an endoscope (or an operation microscope) for observing an operation site and forceps or the like for treating the operation site are put in the retractor.

FIG. 1 is a top view of the retractor inserted into the small incision part and the endoscope put in the retractor. FIG. 2 is a cross-sectional view of the retractor and the endoscope. FIG. 3 is a cross-sectional view of the retractor in which the forceps are put.

As illustrated in the drawings, the endoscope 2 is conventionally fixed to an inner wall of the retractor 1. In this case, an oblique mirror, a visible range 3 of which is shifted sideways from the front in a longitudinal direction, is employed for the endoscope 2 so that the operation site that exists in front of a distal end of the retractor 1 can be captured.

CITATION LIST

Patent Document

Patent Document 1: Japanese Patent Application (Translation of PCT Application) Laid-Open No. 2011-502550

SUMMARY OF THE INVENTION

Problems to be Solved by the Invention

As mentioned above, in a case where the endoscope 2 is fixed to the inner wall of the retractor 1, the endoscope can be brought very close to the operation site. Therefore, the forceps 4 do not easily come into sight, and the operation site can be closely observed.

However, since the endoscope 2 is fixed to the retractor 1, as illustrated in FIG. 3, the endoscope 2 is likely to narrow a movable range of the forceps 4. In addition, in order to adjust the visible range (imaging range) 3 of the endoscope 2, the retractor 1 inserted into a human body is rotated. Therefore, a shape of the retractor 1 needs to be limited to a cylindrical shape to minimize an influence of the rotation of the retractor 1 on the human body.

The present disclosure has been made in consideration of this circumstance in order to be capable of arranging an endoscope so that the endoscope is not fixed to a retractor and has a degree of freedom, and to be capable of correcting an image deterioration such as a blur that might occur in this case.

Solutions to Problems

An image processing device according to a first aspect of the present disclosure is the image processing device configured to correct, frame by frame, a motion image having a predetermined frame rate, and the image processing device includes: a marker detecting unit configured to detect a marker provided on an operation tool and photographed in a current frame; a calculation unit configured to calculate a blur correction amount on the basis of a position of the detected marker; and a blur correction unit configured to perform a blur correction on the current frame in accordance with the blur correction amount.

The motion image can be captured by an imaging device held inside a tubular retractor so as to have a degree of freedom, and the marker can be provided on an inner wall of the retractor serving as the operation tool.

The marker can be provided on an end side of the inner wall of the retractor so as to have a zonal shape.

The imaging device can be an endoscope.

The image processing device according to the first aspect of the present disclosure can further include a motion vector detecting unit configured to detect a motion vector between a frame that precedes the current frame and has undergone the blur correction and the current frame, and the calculation unit can calculate the blur correction amount on the basis of the position of the detected marker, and finely adjust the calculated blur correction amount using the detected motion vector.

The motion vector detecting unit can detect the motion vector by means of pixel matching between the frame that precedes the current frame and has undergone the blur correction and the current frame.

The image processing device according to the first aspect of the present disclosure can further include a motion information acquisition unit configured to acquire motion information of the imaging device, and the motion vector detecting unit can limit a search range of the pixel matching using the acquired motion information.

The image processing device according to the first aspect of the present disclosure can further include: an object region detecting unit configured to detect a region in which a predetermined object that possibly exists on the current frame is photographed; and a replacement unit configured to replace a pixel value of the region of the object in the current frame that has undergone the blur correction using a pixel value of a corresponding region of a frame that precedes the current frame and has undergone the blur correction.

An image processing method according to the first aspect of the present disclosure is the image processing method for an image processing device configured to correct, frame by frame, a motion image having a predetermined frame rate, and the image processing method includes, by the image processing device: a marker detecting step of detecting a marker provided on an operation tool and photographed in a current frame; a calculation step of calculating a blur correction amount on the basis of a position of the detected marker; and a blur correction step of performing a blur correction on the current frame in accordance with the blur correction amount.

A program according to the first aspect of the present disclosure causes a computer configured to correct, frame by frame, a motion image having a predetermined frame rate to function as: a marker detecting unit configured to detect a marker provided on an operation tool and photographed in a current frame; a calculation unit configured to calculate a blur correction amount on the basis of a position of the detected marker; and a blur correction unit configured to perform a blur correction on the current frame in accordance with the blur correction amount.

An endoscope system according to the first aspect of the present disclosure is the endoscope system having an endoscope and an image processing device, the endoscope captures a motion image having a predetermined frame rate and supplies the motion image to the image processing device frame by frame, with the endoscope held inside a tubular retractor so as to have a degree of freedom, and the image processing device includes: a marker detecting unit configured to detect a marker provided on an inner wall of the retractor and photographed in a current frame; a calculation unit configured to calculate a blur correction amount on the basis of a position of the detected marker; and a blur correction unit configured to perform a blur correction on the current frame in accordance with the blur correction amount.

According to the first aspect of the present disclosure, the marker photographed in the current frame is detected, the blur correction amount is calculated on the basis of the position of the detected marker, and the blur correction is performed on the current frame in accordance with the blur correction amount.

An image processing device according to a second aspect of the present disclosure is the image processing device configured to correct, frame by frame, a motion image having a predetermined frame rate, and the image processing device includes: an object region detecting unit configured to detect a region in which a predetermined object that possibly exists on a current frame is photographed; a blur correction unit configured to perform a blur correction on the current frame; and a replacement unit configured to replace a pixel value of the region of the object in the frame that has undergone the blur correction using a pixel value of a corresponding region of a frame that has undergone the blur correction and precedes the frame that has undergone the blur correction.

The motion image can be captured by an imaging device held inside a tubular retractor so as to have a degree of freedom.

The imaging device can be an endoscope, and the predetermined object can be forceps.

The image processing device according to the second aspect of the present disclosure can further include: a marker detecting unit configured to detect a marker provided on an inner wall of the retractor and photographed in the current frame; and a calculation unit configured to calculate a blur correction amount on the basis of a position of the detected marker, and the blur correction unit can perform the blur correction on the current frame in accordance with the blur correction amount.

The image processing device according to the second aspect of the present disclosure can further include a motion information acquisition unit configured to acquire motion information of an imaging device that captures the motion image, and the blur correction unit can perform the blur correction on the current frame on the basis of the motion information.

An image processing method according to the second aspect of the present disclosure is the image processing method for an image processing device configured to correct, frame by frame, a motion image having a predetermined frame rate, and the image processing method includes, by the image processing device: an object region detecting step of detecting a region in which a predetermined object that possibly exists on a current frame is photographed; a blur correction step of performing a blur correction on the current frame; and a replacement step of replacing a pixel value of the region of the object in the frame that has undergone the blur correction using a pixel value of a corresponding region of a frame that has undergone the blur correction and precedes the frame that has undergone the blur correction.

A program according to the second aspect of the present disclosure causes a computer configured to correct, frame by frame, a motion image having a predetermined frame rate to function as: an object region detecting unit configured to detect a region in which a predetermined object that possibly exists on a current frame is photographed; a blur correction unit configured to perform a blur correction on the current frame; and a replacement unit configured to replace a pixel value of the region of the object in the frame that has undergone the blur correction using a pixel value of a corresponding region of a frame that has undergone the blur correction and precedes the frame that has undergone the blur correction.

An endoscope system according to the second aspect of the present disclosure is the endoscope system having an endoscope and an image processing device, the endoscope captures a motion image having a predetermined frame rate and supplies the motion image to the image processing device frame by frame, with the endoscope held inside a tubular retractor so as to have a degree of freedom, and the image processing device includes: an object region detecting unit configured to detect a region in which a predetermined object that possibly exists on a current frame is photographed; a blur correction unit configured to perform a blur correction on the current frame; and a replacement unit configured to replace a pixel value of the region of the object in the frame that has undergone the blur correction using a pixel value of a corresponding region of a frame that has undergone the blur correction and precedes the frame that has undergone the blur correction.

According to the second aspect of the present disclosure, the region in which the predetermined object that possibly exists on the current frame is photographed is detected, the blur correction is performed on the current frame, and the pixel value of the region of the object in the frame that has undergone the blur correction is replaced using the pixel value of the corresponding region of the frame that has undergone the blur correction and precedes the frame that has undergone the blur correction.

Effects of the Invention

According to a first aspect of the present disclosure, it is possible to correct a blur of a motion image captured by an imaging device or the like arranged so as to have a degree of freedom without being fixed to a retractor.

According to a second aspect of the present disclosure, it is possible to correct forceps or the like that are possibly photographed in a motion image captured by an imaging device or the like arranged so as to have a degree of freedom without being fixed to a retractor, so that the forceps are made inconspicuous.

BRIEF DESCRIPTION OF DRAWINGS

FIG. 10 is a diagram illustrating a positional relation between a marker center point and an affected area image center point or the like.

MODE FOR CARRYING OUT THE INVENTION

Hereinafter, the best mode for carrying out the present disclosure (hereinafter referred to as an embodiment) will be described in detail with reference to the drawings.

<Arrangement of Endoscope on Retractor>

First, an arrangement of a retractor (operation tool) and an endoscope employed in the present disclosure will be described with reference to FIGS. 4 to 6.

Figure 1:
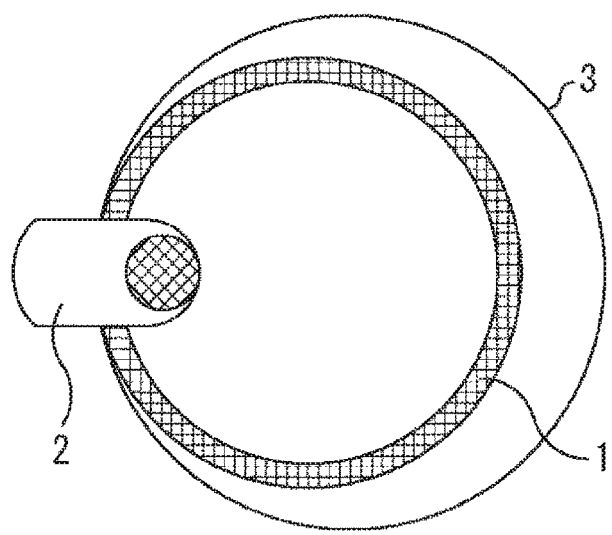
FIG. 1 is a top view of a conventional retractor to which an endoscope is fixed.
Figure 2:
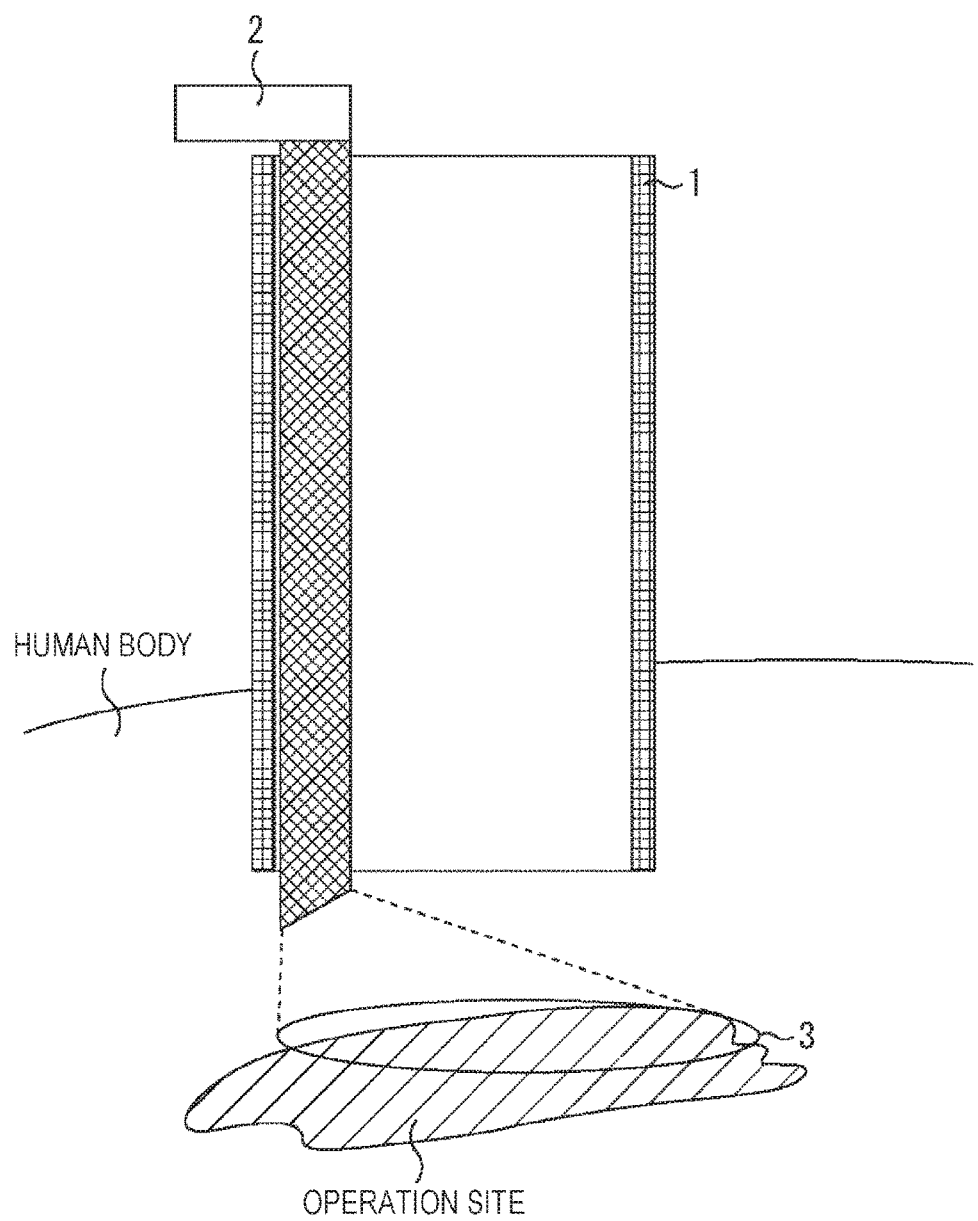
FIG. 2 is a cross-sectional view of the conventional retractor to which the endoscope is fixed.
Figure 3:
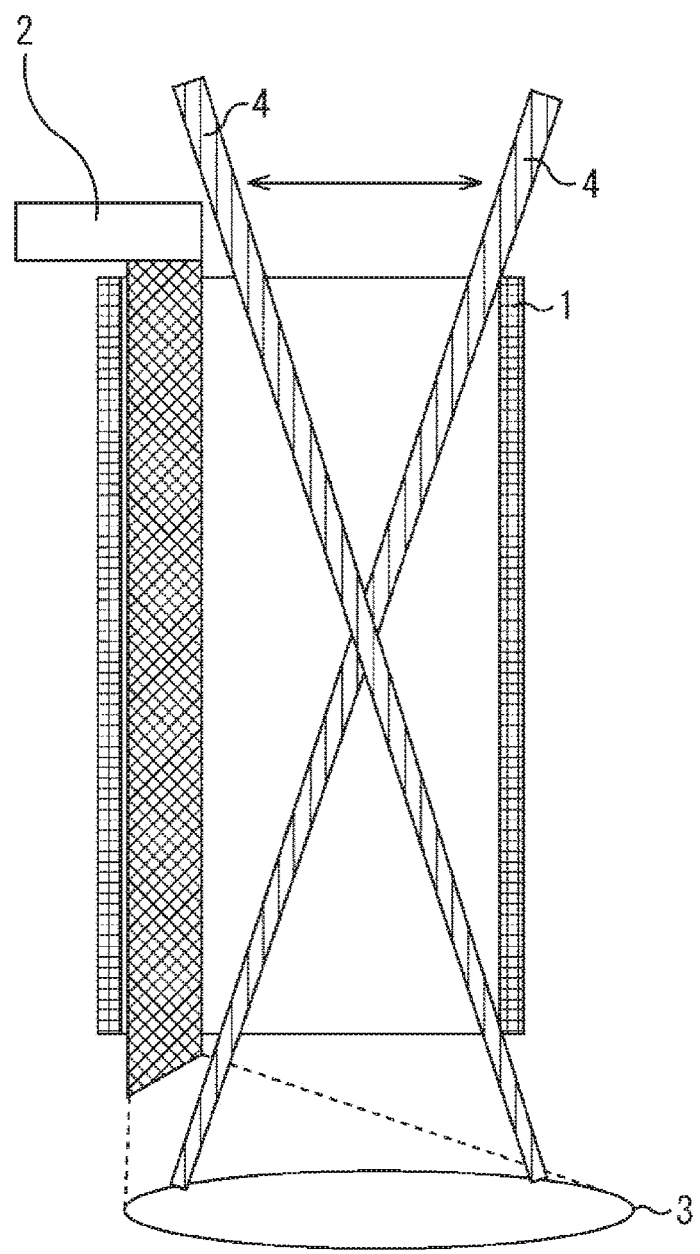
FIG. 3 is a cross-sectional view illustrating a movable range of forceps in the conventional retractor to which the endoscope is fixed.
Figure 4:
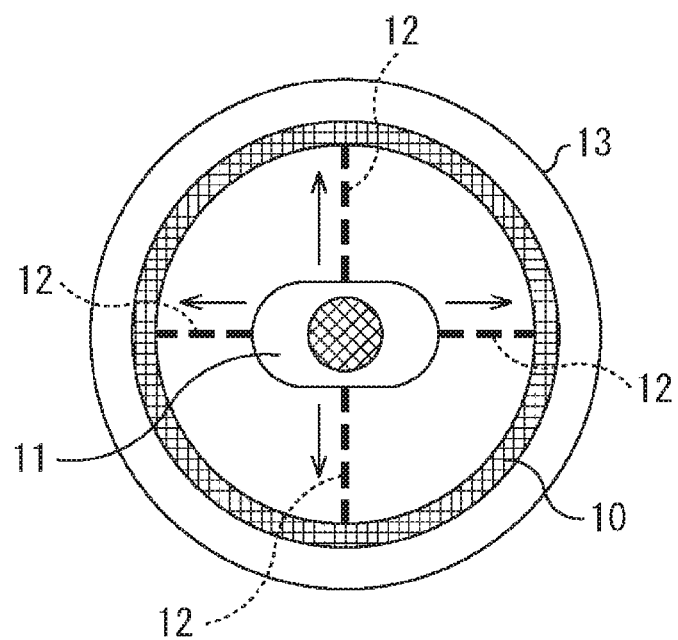
FIG. 4 is a top view of a tractor and an endoscope employed in the present disclosure.

FIG. 4 is a top view of the retractor and the endoscope employed in the present disclosure. FIG. 5 is a cross-sectional view of the retractor and the endoscope. FIG. 6 is a cross-sectional view of the retractor in which forceps are put.

As illustrated in FIG. 4, the endoscope 11 is held inside the retractor 10 so as to have a degree of freedom via a support part 12 made of an elastic material. Therefore, a user (a doctor or the like who performs an operation) can parallelly move the endoscope 11 to an arbitrary position inside the retractor 10. However, since a visible range (imaging range) 13 of the endoscope 11 moves as the endoscope 11 is parallelly moved, a captured motion image needs to be corrected.

Figure 5:
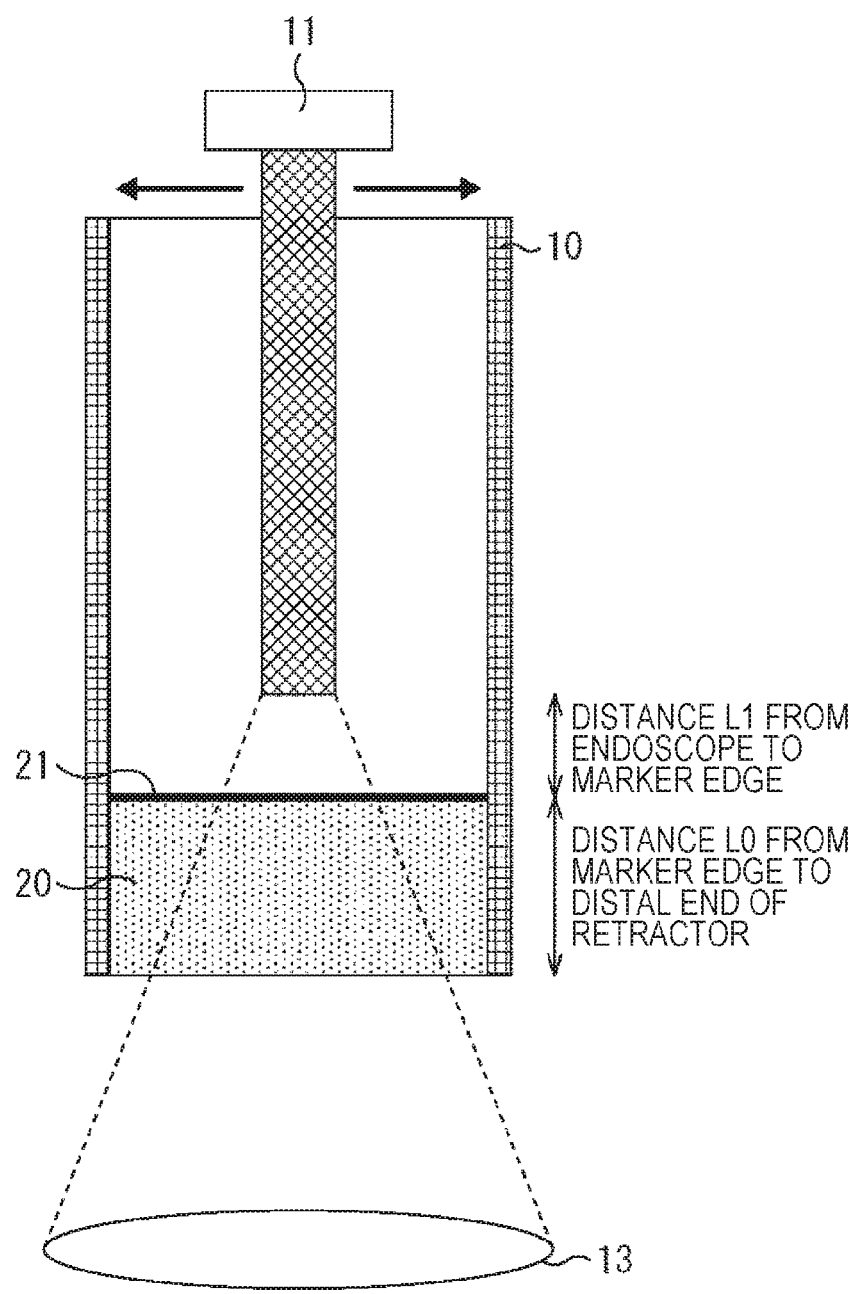
FIG. 5 is a cross-sectional view of the retractor and the endoscope employed in the present disclosure.

As illustrated in FIG. 5, a zonal marker 20 having a width L0 is provided on an inner wall of the retractor 10 on a lower end side. The marker 20 is configured such that the inner wall of the retractor 10 is colored, for example, in black by printing, vapor deposition or the like. A part of the inner wall other than the marker 20 is achromatic or colored in a color that can be distinguished from that of the marker 20. In particular, an upper end of the marker 20 is referred to as a marker edge 21. Alternatively, only the marker edge 21 may be provided.

As for the endoscope 11, an endoscope having such a length that a lower end of the endoscope is located above the marker edge 21 while the endoscope is held inside the retractor 10 is employed. Consequently, a distance between a lens arranged at the lower end of the endoscope 11 and an operation site increases, whereby an angle of view of the lens can be narrowed. Therefore, the endoscope 11 that is advantageous to both an amount of light and image quality can be employed.

Meanwhile, marker information representing a position of the marker edge 21 is measured in advance and held in a marker information holding unit 67 (FIG. 7) of an image processing device 51 which will be described later. The marker information is specifically a distance L0 from the lower end of the retractor 10 to the marker edge 21 and a distance L1 from the lower end of the endoscope 11 to the marker edge 21.

Figure 6:
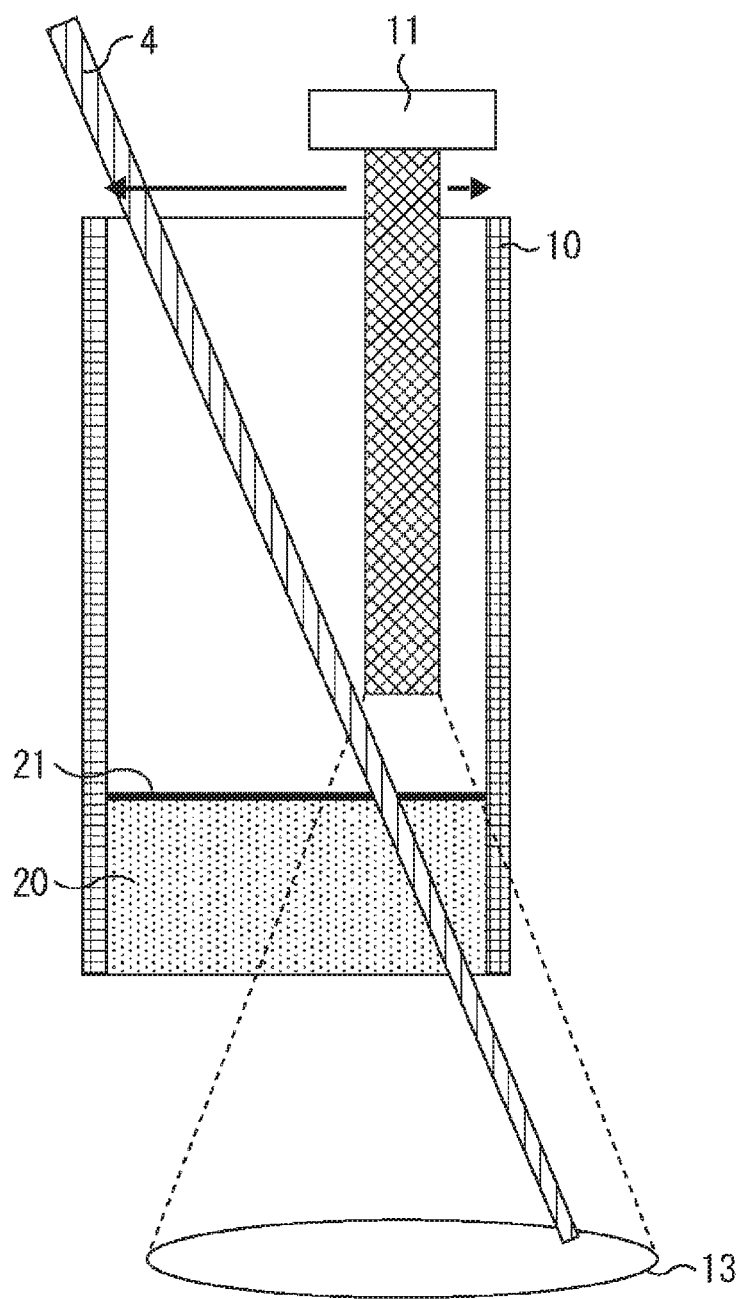
FIG. 6 is a cross-sectional view of the retractor employed in the present disclosure in which forceps are put.

In addition, as illustrated in FIG. 6, in a case where forceps 4 are put in the retractor 10, the endoscope 11 can be shifted inside the retractor 10 when the forceps 4 are moved. Therefore, it is possible to inhibit a movable range of the forceps 4 from being narrowed by the presence of the endoscope 11. It is also possible to employ the retractor 10 having a relatively narrow diameter.

Furthermore, when the visible range 13 of the endoscope 11 is adjusted, it is possible to move the endoscope 11 without rotating the retractor 10 itself inserted into a human body unlike the conventional technique. Therefore, a shape of the retractor 10 does not need to be limited to a cylindrical shape. In other words, the shape of the retractor 10 only needs to be a tubular shape, and may be, for example, an ellipse cylindrical shape or a square tubular shape.

<Exemplary Configuration of Endoscope System 50 to which Present Disclosure is Applied>

Figure 7:
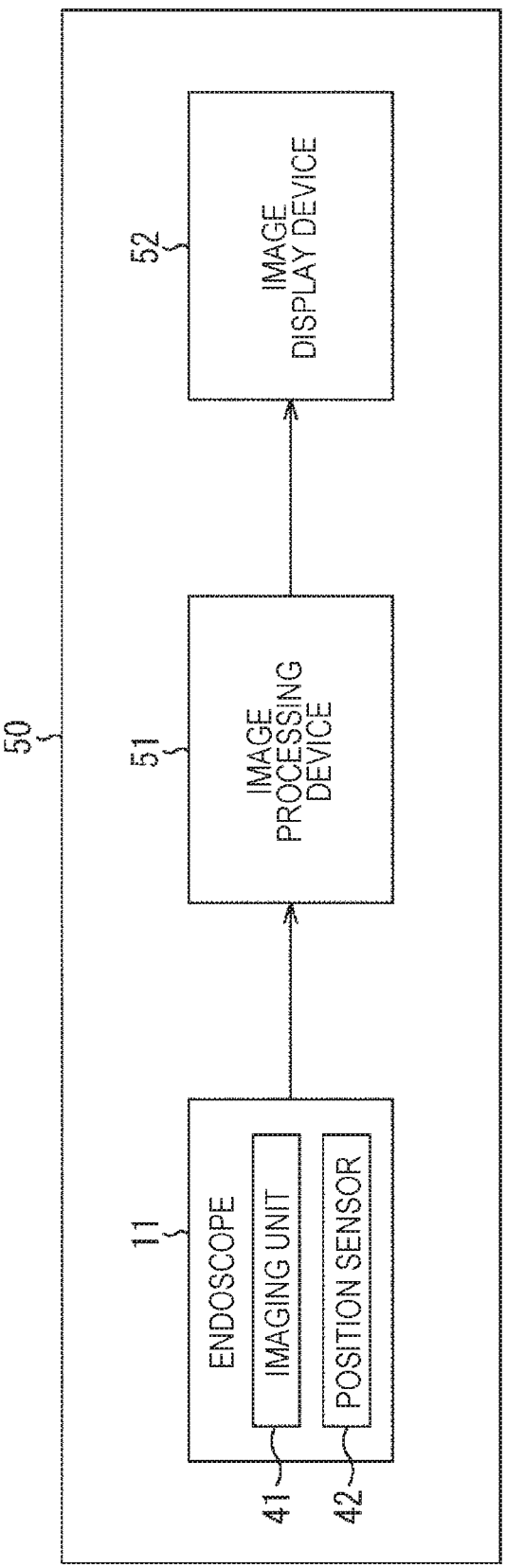
FIG. 7 is a block diagram illustrating an exemplary configuration of an endoscope system to which the present disclosure is applied.

Next, an exemplary configuration of an endoscope system 50 to which the present disclosure is applied is illustrated in FIG. 7. The endoscope system 50 includes the endoscope 11, the image processing device 51, and an image display device 52.

As illustrated in FIGS. 4 to 6, the endoscope 11 is held inside the retractor 10 so as to have the degree of freedom.

The endoscope 11 has an imaging unit 41 and a position sensor 42. The imaging unit 41 outputs, on a frame-by-frame basis to the image processing device 51, a motion image having a predetermined frame rate (for example, 30 to 120 fps) obtained as the result of the capture. The position sensor 42 detects a motion of the endoscope 11, and outputs, to the image processing device 51, position sensor information representing the motion of the endoscope 11.

The image processing device 51 performs a blur correction or the like on each frame of the motion image input from the endoscope 11, and outputs the corrected frame to the image display device 52. The image display device 52 includes a liquid crystal display or the like, and presents, to the user, a screen of the frame sequentially input from the image processing device 51.

<Exemplary Configuration of Image Processing Device 51 According to Embodiment of Present Disclosure>

Figure 8:
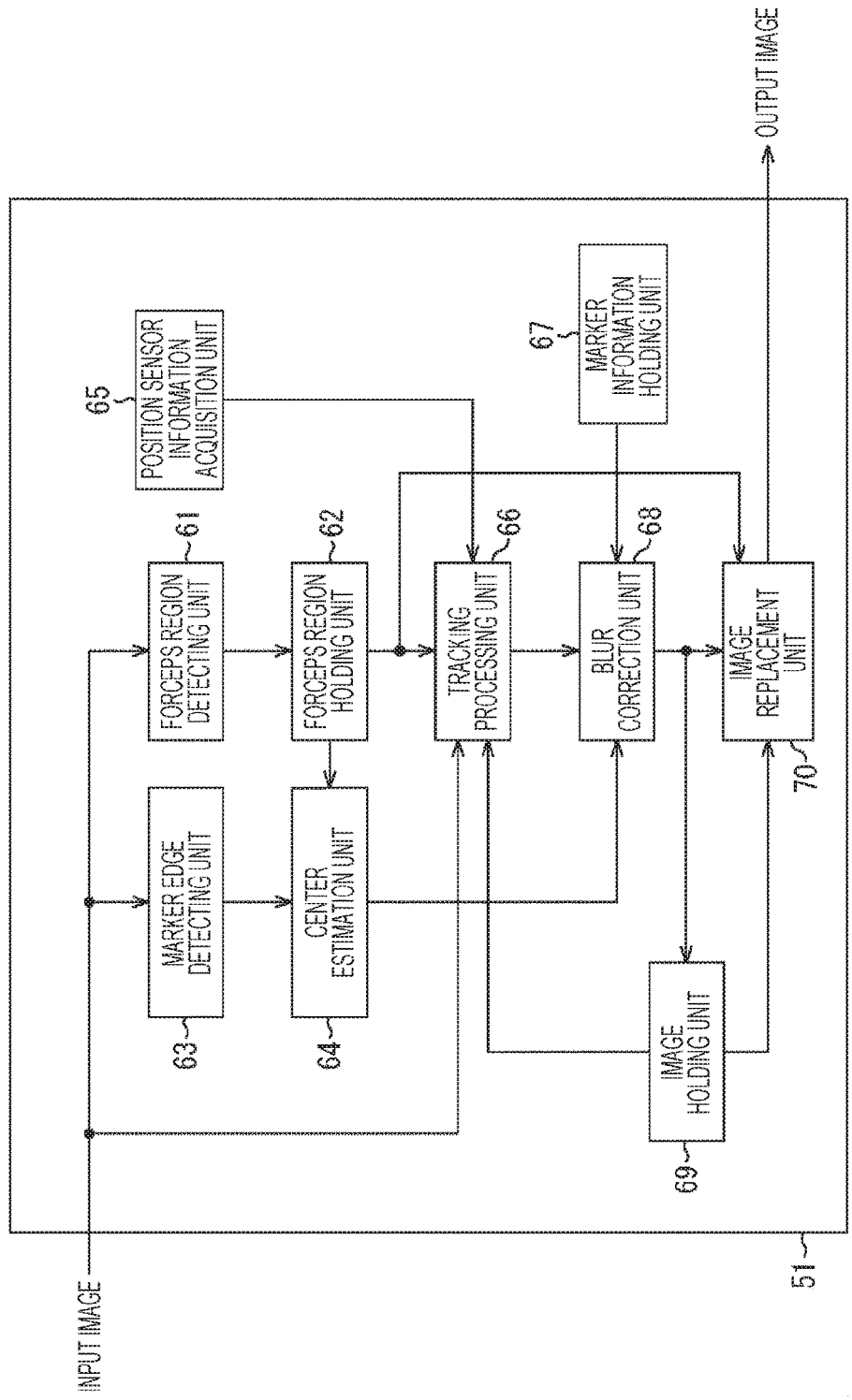
FIG. 8 is a block diagram illustrating an exemplary detailed configuration of an image processing device in FIG. 7.

Next, an exemplary configuration of the image processing device 51 according to an embodiment of the present disclosure is illustrated in FIG. 8.

The image processing device 51 includes a forceps region detecting unit 61, a forceps region holding unit 62, a marker edge detecting unit 63, a center estimation unit 64, a position sensor information acquisition unit 65, a tracking processing unit 66, the marker information holding unit 67, a blur correction unit 68, an image holding unit 69, and a replacement unit 70.

In the image processing device 51, each frame of the motion image input from the imaging unit 41 of the endoscope 11 is supplied to the forceps region detecting unit 61, the marker edge detecting unit 63, and the tracking processing unit 66.

Figure 9:
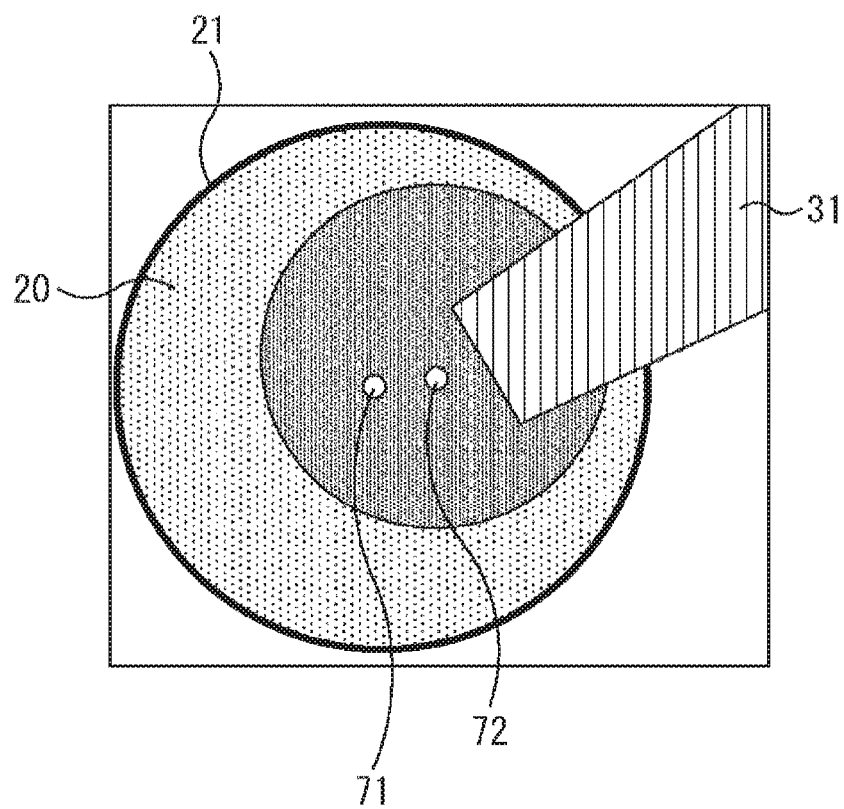
FIG. 9 is a diagram illustrating an exemplary display of one frame of motion image data.

The forceps region detecting unit 61 detects, from the frame supplied from a former stage such as a frame illustrated in FIG. 9, a forceps region 31 in which the forceps 4 are photographed. The forceps region detecting unit 61 then notifies the forceps region holding unit 62 of coordinate information of the forceps region 31. Any existing technique can be applied to the detection of the forceps region 31. For example, a chroma key technique can be applied. Specifically, the forceps 31 are subjected to a surface treatment using a hue (for example, blue) that is different from both that of the operation site of the human body and that of the inner wall of the retractor 10, and the forceps region 31 is detected on the basis of the hue. Note that the forceps region 31 may be detected from all the frames, or may be detected at intervals of a few frames.

The forceps region holding unit 62 temporarily holds the coordinate information of the forceps region 31, and supplies the coordinate information in response to a request from a later stage.

The marker edge detecting unit 63 detects the marker edge 21 from the frame supplied from a former stage such as the frame illustrated in FIG. 9. The marker edge detecting unit 63 then notifies the center estimation unit 64 of coordinate information of the marker edge 21. Note that the marker edge 21 can be detected on the basis of a drastic change of color or luminance in the marker 20 on the inner wall of the retractor 10 and the other region.

The center estimation unit 64 detects, on the frame, a circle (or an ellipse) corresponding to the marker edge 21 by interpolating and connecting the coordinates of the detected marker edge 21. A least squares method, a Hough transform or the like can be used for the detection of the circle or the like. In this case, the coordinates included in the forceps region may be excluded from the coordinates of the detected marker edge 21. The center estimation unit 64 also estimates center coordinates of the detected circle or the like (hereinafter referred to as a marker center point 71), and notifies the blur correction unit 68 of the marker center point 71 together with center coordinates of the frame (hereinafter referred to as an image center point 72).

Meanwhile, in a case where the endoscope 11 is located in the center of the retractor 10, the marker center point 71 and the image center point 72 coincide. However, in a case where the endoscope 11 is displaced from the center of the retractor 10, a gap occurs between the marker center point 71 and the image center point 72. Therefore, when the blur correction for keeping a position of the operation site in the frame fixed is performed on the basis of an amount of the gap between the marker center point 71 and the image center point 72, a frame that is captured while the endoscope 11 is fixed to the center of the retractor 10 can be obtained. This blur correction is performed in the blur correction unit 68 which will be described later.

The position sensor information acquisition unit 65 acquires the position sensor information from the position sensor 42 embedded in the endoscope 11. The position sensor information acquisition unit 65 then estimates the position of the endoscope 11 on the basis of the position sensor information, and outputs the position of the endoscope 11 to the tracking processing unit 66. The tracking processing unit 66 performs, in the vicinity of the image center point 72, pixel matching between a current frame input from the imaging unit 41 of the endoscope 11 and a previous frame that has undergone the blur correction and is held in the image holding unit 69. When the pixel matching is performed, the forceps region 31 can be excluded. In addition, a search range of the pixel matching can be limited on the basis of the position of the endoscope 11. The position sensor information is used for the pixel matching, whereby the pixel matching can be quickly executed. The tracking processing unit 66 outputs, to the blur correction unit 68, a motion vector obtained as the result of the pixel matching and the current frame. Alternatively, the pixel matching may be performed without using the position sensor information. To the contrary, the pixel matching may not be performed, and the motion vector may be estimated on the basis of only the position sensor information.

The marker information holding unit 67 holds the marker information (specifically, the distances L0, L1 illustrated in FIG. 10) representing a position of the marker 20 on the retractor 10, and supplies the marker information in response to a request from the blur correction unit 68. Meanwhile, in a case where there are several kinds of retractors 10 and endoscopes 11, a plurality of items of marker information that depends on combinations of the retractors 10 and the endoscopes 11 is held in the marker information holding unit 67. Therefore, the marker information that depends on the combination of the retractor 10 and the endoscope 11 for use can be supplied to the center estimation unit 64.

The blur correction unit 68 calculates a blur correction amount on the basis of the marker center point 71 and the image center point 72 of which the blur correction unit 68 is notified by the center estimation unit 64, and on the basis of the marker information acquired from the marker information holding unit 67. The calculation of the blur correction amount will be described with reference to FIG. 10.

Figure 10:
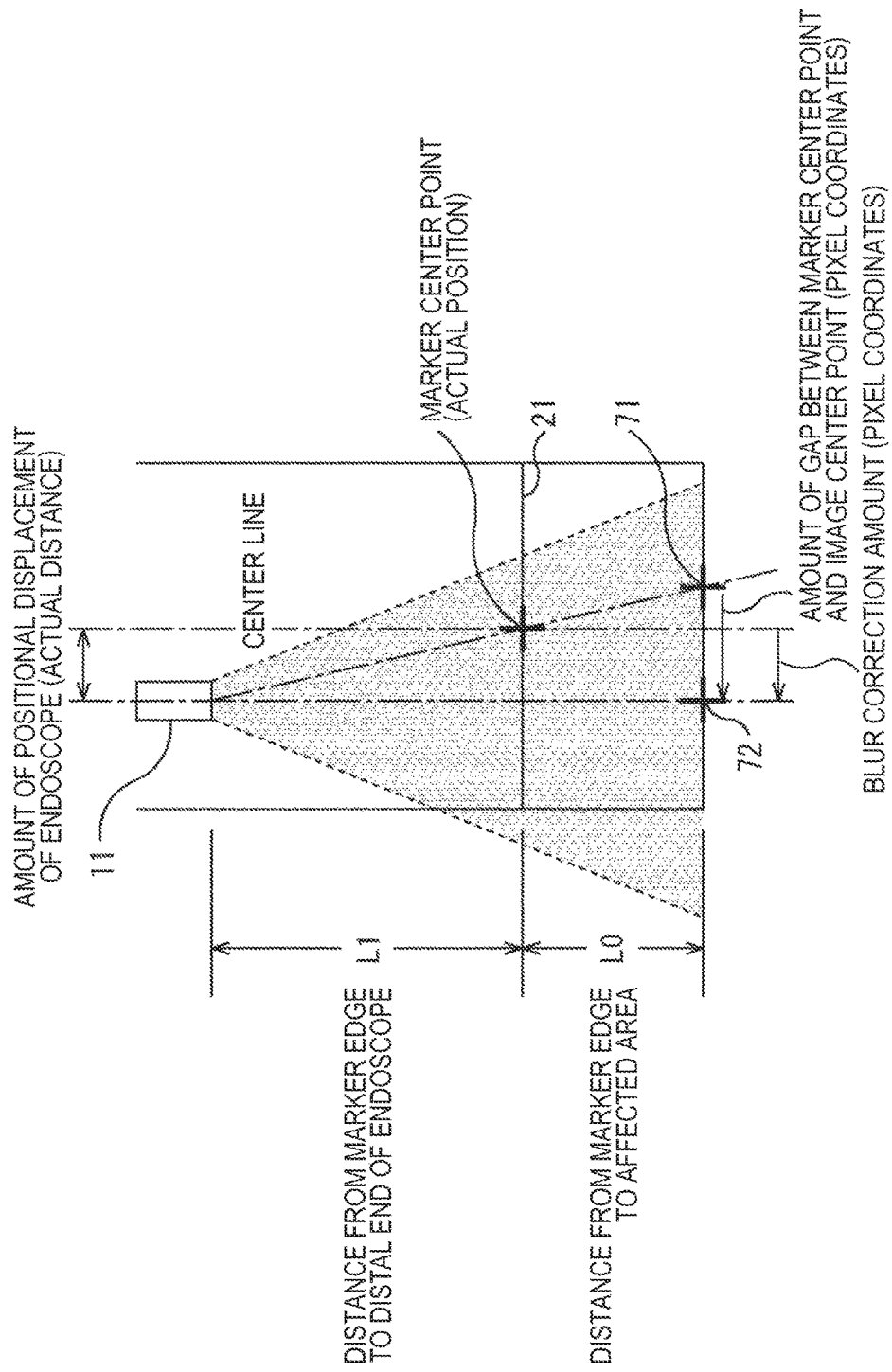

A relation between the marker center point 71, the image center point 72, the distances L0, L1, and the blur correction amount is illustrated in FIG. 10.

As illustrated in FIG. 10, a relation blur correction amount: (amount of gap between marker center point 71 and image center point 72)=L1: (L1+L0) is satisfied. Therefore, the blur correction amount is calculated using the following Formula (1).

$$\text{blur correction amount} = (\text{amount of gap between marker center point 71 and image center point 72}) \times L1/(L1+L0) \quad (1)$$

Furthermore, the blur correction unit 68 finely adjusts the blur correction amount on the basis of the motion vector input from the tracking processing unit 66. The fine adjustment of the blur correction amount based on the motion vector may be performed in such a manner that the motion vector is added to the blur correction amount calculated on the basis of the marker center point 71 or the like, or may be performed in such a manner that the motion vector is weighted, that is, multiplied by a coefficient of 0 to 1.0, and then added. The blur correction unit 68 shifts the current frame in accordance with the determined blur correction amount to perform the blur correction. The blur correction unit 68 then outputs the frame after the blur correction to the image holding unit 69 and the replacement unit 70. Alternatively, in the blur correction unit 68, the blur correction may be performed on the basis of only the position sensor information.

The image holding unit 69 temporarily holds the frame after the blur correction, and supplies the held frame in response to requests from the tracking processing unit 66 and the replacement unit 70.

The replacement unit 70 acquires, from the forceps region holding unit 62, the coordinate information of the forceps region 31 in the current frame after the blur correction. The replacement unit 70 then replaces a pixel value of the forceps region 31 using a pixel value of a previous frame including the corresponding region that has not been the forceps region 31. More specifically, the pixel value of the forceps region 31 in the current frame after the blur correction is replaced by a weighted average value of the pixel value and a pixel value of a previous frame including the corresponding region that is not the forceps region 31 among the previous frames held in the image holding unit 69. A frame to be output to a later stage is generated in this manner. Meanwhile, when the weighted average is calculated, a coefficient is changed in accordance with an interval between the frames that are used for the calculation of the weighted average.

For example, in a case where the weighted average is calculated using a pixel value that precedes by one frame, weighted average value=0.1×pixel value of current frame+0.9×pixel value that precedes by one frame is satisfied.

For example, in a case where the weighted average is calculated using a pixel value that precedes by two frames, weighted average value=0.2×pixel value of current frame+0.8×pixel value that precedes by two frames is satisfied.

For example, in a case where the weighted average is calculated using a pixel value that precedes by three frames, weighted average value=0.3×pixel value of current frame+0.7×pixel value that precedes by three frames is satisfied. Consequently, it is possible to obtain a frame including the forceps region 31 that looks inconspicuous and as if the forceps region 31 melted into the operation site.

However, in a case where the previous frame including the region corresponding to the forceps region 31 in the current frame after the blur correction that is not the forceps region is not held in the image holding unit 69, the replacement of the forceps region 31 is not performed.

<Correction Process by Image Processing Device 51>

Figure 11:
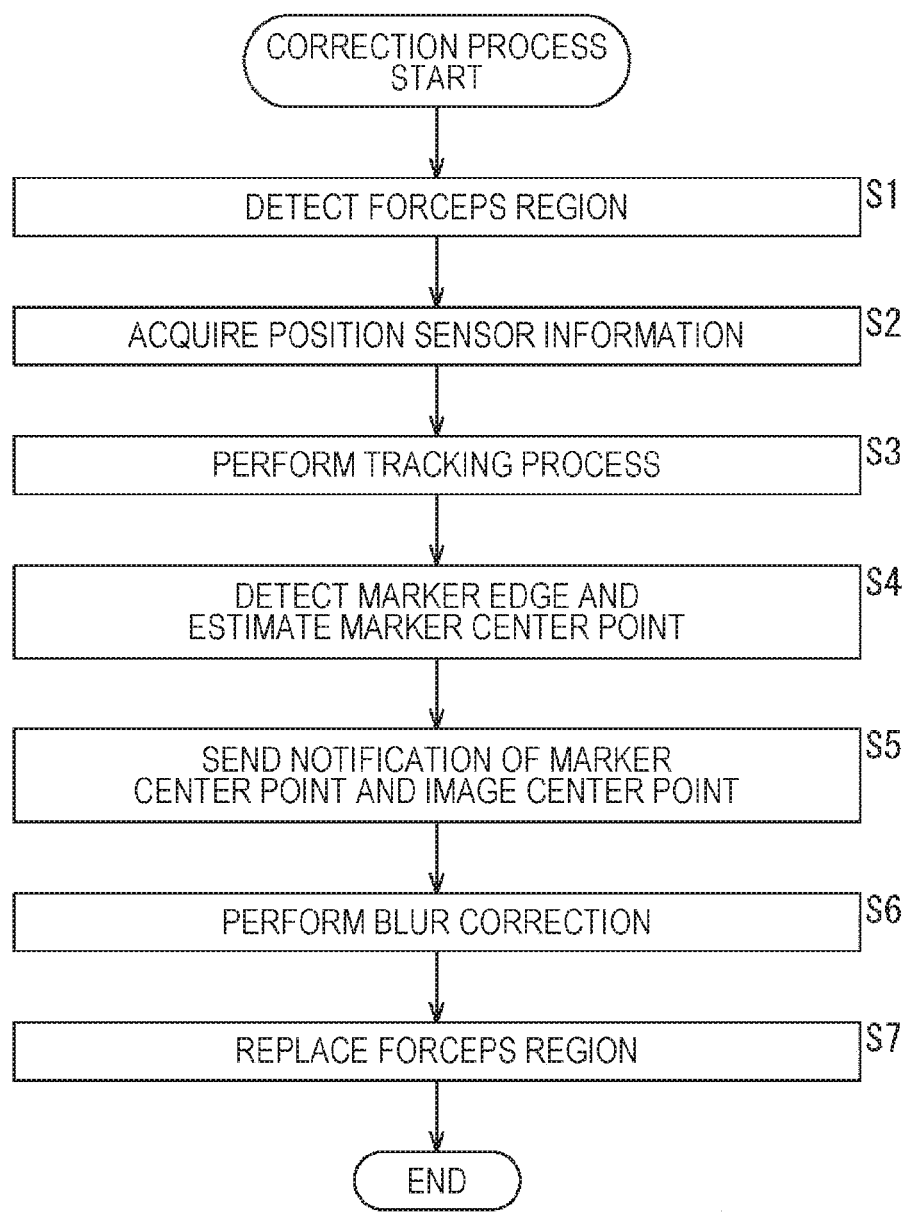
FIG. 11 is a flowchart explaining a correction process.

FIG. 11 is a flowchart explaining a correction process by the image processing device 51 (hereinafter referred to as a first correction process).

The first correction process is executed on each frame of the motion image input from the imaging unit 41 of the endoscope 11 to the image processing device 51.

In step S1, the forceps region detecting unit 61 detects the forceps region 31 in the current frame input from a former stage, and causes the forceps region holding unit 62 to hold the coordinate information of the forceps region 31. In step S2, the position sensor information acquisition unit 65 acquires the position sensor information from the position sensor 42 of the endoscope 11. The position sensor information acquisition unit 65 then estimates the position of the endoscope 11 on the basis of the position sensor information, and outputs the position of the endoscope 11 to the tracking processing unit 66. In step S3, the tracking processing unit 66 performs, in the vicinity of the image center point 72, the pixel matching between the current frame input from the imaging unit 41 of the endoscope 11 and the previous frame (for example, a frame that precedes by one frame) that has undergone the blur correction and is held in the image holding unit 69. The tracking processing unit 66 then detects the motion vector of the current frame with respect to the previous frame, and outputs the motion vector and the current frame to the blur correction unit 68.

In step S4, the marker edge detecting unit 63 detects the marker edge 21 in the frame supplied from a former stage. The marker edge detecting unit 63 then notifies the center estimation unit 64 of the coordinate information of the marker edge 21. The center estimation unit 64 detects, on the frame, the circle (or the ellipse) corresponding to the marker edge 21 by interpolating and connecting the coordinates of the detected marker edge 21. The center estimation unit 64 then estimates the marker center point 71 representing the center coordinates of the circle (or the ellipse). In step S5, the marker edge detecting unit 63 notifies the blur correction unit 68 of the marker center point 71 and the image center point 72 representing the center coordinates of the frame.

Note that the above-mentioned processes in steps S1 to S3 and the processes in steps S4 and S5 are parallelly executed in practice.

In step S6, the blur correction unit 68 acquires the marker information from the marker information holding unit 67, and calculates the blur correction amount by applying, to Formula (1), the acquired marker information as well as the marker center point 71 and the image center point 72 of which the blur correction unit 68 has been notified by the center estimation unit 64. The blur correction unit 68 also finely adjusts the blur correction amount on the basis of the motion vector input from the tracking processing unit 66, and performs the blur correction on the current frame. The blur correction unit 68 then outputs the frame after the blur correction to the image holding unit 69 and the replacement unit 70.

In step S7, the replacement unit 70 replaces the pixel value of the forceps region 31 in the current frame after the blur correction using the pixel value of the previous frame including the corresponding region that has not been the forceps region 31. The replacement unit 70 then outputs the frame to a later stage. This is the end of the description of the first correction process for the one frame of the sequentially input motion image.

According to the above-described first correction process, the blur correction amount calculated on the basis of the detected marker edge 21 is finely adjusted using the motion vector between the temporally successive frames, and the correction is performed after that. Therefore, the blur correction can be performed with a high degree of accuracy.

Figure 12:
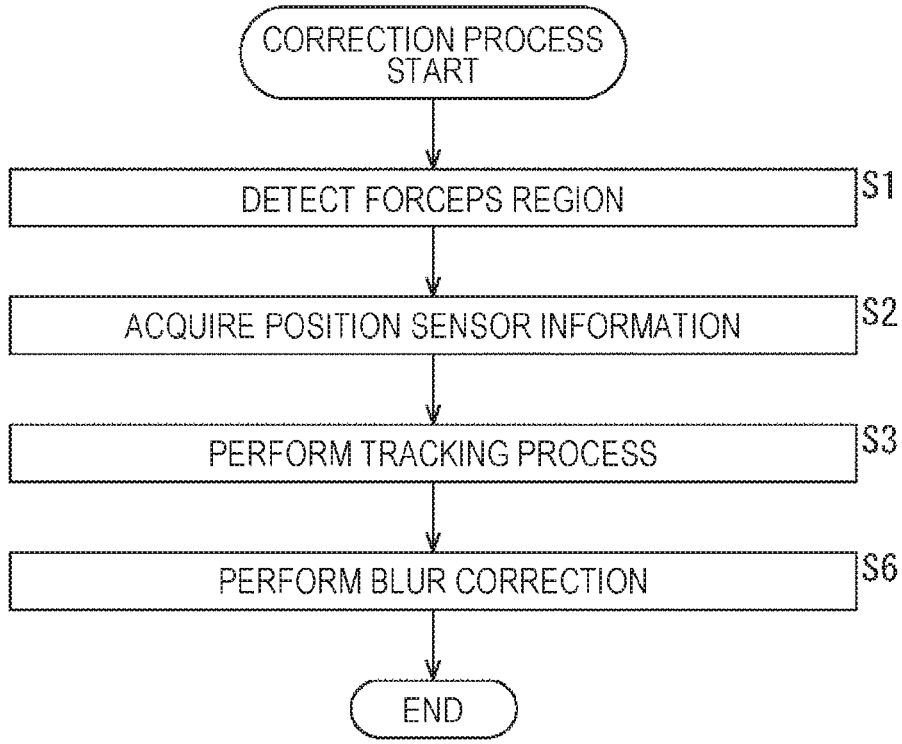
FIG. 12 is a flowchart explaining another correction process.

Next, FIG. 12 is a flowchart explaining another correction process by the image processing device 51 (hereinafter referred to as a second correction process).

The second correction process is such a process that the processes in steps S4, S5, and S7 are omitted from the first correction process described above with reference to FIG. 11. In other words, in the second correction process, the detection of the marker edge 21, the calculation of the blur correction amount based on the detection, and the replacement of the forceps region 31 in the frame that has undergone the blur correction are omitted.

According to the second correction process, a simplified blur correction can be performed on the basis of only the motion vector between the temporally successive frames that is output from the tracking processing unit 66.

Figure 13:
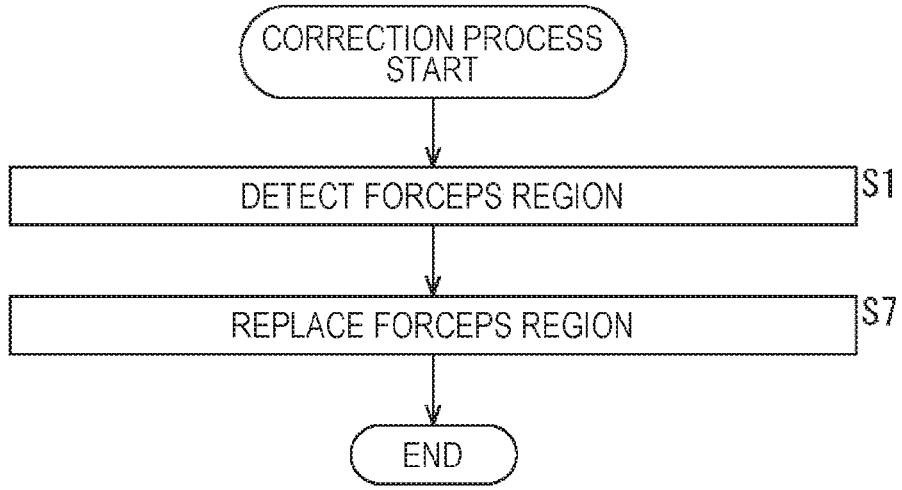
FIG. 13 is a flowchart explaining still another correction process.
Figure 14:
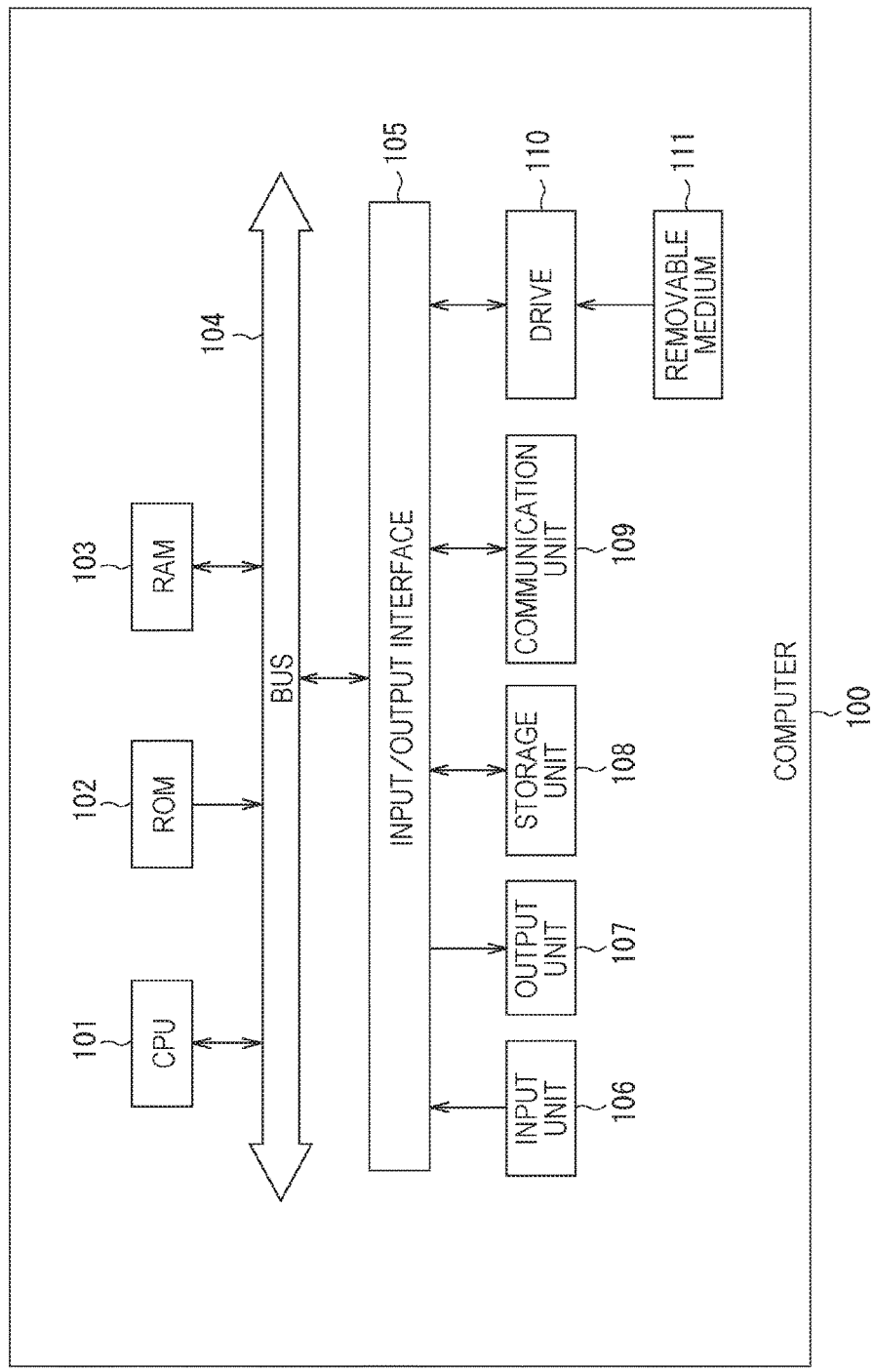
FIG. 14 is a block diagram illustrating an exemplary configuration of a computer.

Next, FIG. 13 is a flowchart explaining still another correction process by the image processing device 51 (hereinafter referred to as a third correction process).

The third correction process is such a process that the processes in steps S2 to S6 are omitted from the first correction process described above with reference to FIG. 11. In other words, according to the third correction process, the replacement of the forceps region 31 in the current frame is performed.

Additionally, the motion image to be processed by the above-mentioned image processing device 51 is not limited to the motion image output from the endoscope 11, and may be, for example, a motion image output from an operation microscope.

The above-mentioned sequence of processes can be executed by hardware, and can also be executed by software. In a case where the sequence of processes is executed by the software, a program constituting the software is installed on a computer. As used herein, the computer includes a computer incorporated in dedicated hardware or, for example, a general personal computer or the like that can install various programs to execute various functions.

FIG. 12 is a block diagram illustrating an exemplary configuration of the hardware of the computer that executes the above-mentioned sequence of processes by means of the program.

The computer 100 may be arranged in an operation room in which the endoscope 11 and the image display device 52 are arranged, or may be arranged in a remote location that can be connected to the endoscope 11 and the image display device 52 via a network that is represented by the Internet.

In the computer 100, a central processing unit (CPU) 101, a read only memory (ROM) 102, and a random access memory (RAM) 103 are coupled to one another by a bus 104.

An input/output interface 105 is further connected to the bus 104. An input unit 106, an output unit 107, a storage unit 108, a communication unit 109, and a drive 110 are connected to the input/output interface 105.

The input unit 106 includes a keyboard, a mouse, and a microphone or the like. The output unit 107 includes a display and a speaker or the like. The storage unit 108 includes a hard disc, a non-volatile memory or the like. The communication unit 109 includes a network interface or the like. The drive 110 drives a removable medium 111 such as a magnetic disc, an optical disc, a magneto-optical disc, or a semiconductor memory.

In the computer 100 configured as mentioned above, the above-mentioned sequence of processes is performed in such a manner that, for example, the CPU 101 loads the program stored in the storage unit 108 on the RAM 103 via the input/output interface 105 and the bus 104, and executes the program.

Note that the program that is executed by the computer 100 may be such a program that the processes are performed in time series in the order described in the present description, or may be such a program that the processes are performed parallelly or at a necessary timing, i.e., for example, when a call is performed.

The embodiment of the present disclosure is not limited to the above-mentioned embodiment, and can be variously changed in a range not departing from the gist of the present disclosure.

The present disclosure can also be configured as follows.

(1)

An image processing device configured to correct, frame by frame, a motion image having a predetermined frame rate, the image processing device including:

a marker detecting unit configured to detect a marker provided on an operation tool and photographed in a current frame;

a calculation unit configured to calculate a blur correction amount on the basis of a position of the detected marker; and a blur correction unit configured to perform a blur correction on the current frame in accordance with the blur correction amount.

(2)

The image processing device according to (1), wherein the motion image is captured by an imaging device held inside a tubular retractor so as to have a degree of freedom, and the marker is provided on an inner wall of the retractor serving as the operation tool.

(3)

The image processing device according to (2), wherein the marker is provided on an end side of the inner wall of the retractor so as to have a zonal shape.

(4)

The image processing device according to (2) or (3), wherein the imaging device is an endoscope.

(5)

The image processing device according to any of (1) to (4), further including a motion vector detecting unit configured to detect a motion vector between a frame that precedes the current frame and has undergone the blur correction and the current frame, wherein the calculation unit calculates the blur correction amount on the basis of the position of the detected marker, and finely adjusts the calculated blur correction amount using the detected motion vector.

(6)

The image processing device according to (5), wherein the motion vector detecting unit detects the motion vector by means of pixel matching between the frame that precedes the current frame and has undergone the blur correction and the current frame.

(7)

The image processing device according to (6), further including a motion information acquisition unit configured to acquire motion information of the imaging device, wherein the motion vector detecting unit limits a search range of the pixel matching using the acquired motion information.

(8)

The image processing device according to any of (1) to (7), further including:

an object region detecting unit configured to detect a region in which a predetermined object that possibly exists on the current frame is photographed; and a replacement unit configured to replace a pixel value of the region of the object in the current frame that has undergone the blur correction using a pixel value of a corresponding region of a frame that precedes the current frame and has undergone the blur correction.

(9)

An image processing method for an image processing device configured to correct, frame by frame, a motion image having a predetermined frame rate, the image processing method including, by the image processing device:

a marker detecting step of detecting a marker provided on an operation tool and photographed in a current frame;

a calculation step of calculating a blur correction amount on the basis of a position of the detected marker; and a blur correction step of performing a blur correction on the current frame in accordance with the blur correction amount.

(10)

A program that causes a computer configured to correct, frame by frame, a motion image having a predetermined frame rate to function as:

a marker detecting unit configured to detect a marker provided on an operation tool and photographed in a current frame;

a calculation unit configured to calculate a blur correction amount on the basis of a position of the detected marker; and a blur correction unit configured to perform a blur correction on the current frame in accordance with the blur correction amount.

(11)

An endoscope system having an endoscope and an image processing device, wherein the endoscope captures a motion image having a predetermined frame rate and supplies the motion image to the image processing device frame by frame, with the endoscope held inside a tubular retractor so as to have a degree of freedom, and the image processing device includes:

a marker detecting unit configured to detect a marker provided on an inner wall of the retractor and photographed in a current frame;

a calculation unit configured to calculate a blur correction amount on the basis of a position of the detected marker; and a blur correction unit configured to perform a blur correction on the current frame in accordance with the blur correction amount.

(12)

An image processing device configured to correct, frame by frame, a motion image having a predetermined frame rate, the image processing device including:

an object region detecting unit configured to detect a region in which a predetermined object that possibly exists on a current frame is photographed;

a blur correction unit configured to perform a blur correction on the current frame; and a replacement unit configured to replace a pixel value of the region of the object in the frame that has undergone the blur correction using a pixel value of a corresponding region of a frame that has undergone the blur correction and precedes the frame that has undergone the blur correction.

(13)

The image processing device according to (12), wherein the motion image is captured by an imaging device held inside a tubular retractor so as to have a degree of freedom.

(14)

The image processing device according to (13), wherein the imaging device is an endoscope, and the predetermined object is forceps.

(15)

The image processing device according to any of (12) to (14), further including:

a marker detecting unit configured to detect a marker provided on an inner wall of the retractor and photographed in the current frame; and a calculation unit configured to calculate a blur correction amount on the basis of a position of the detected marker, wherein the blur correction unit performs the blur correction on the current frame in accordance with the blur correction amount.

(16)

The image processing device according to any of (12) to (14), further including a motion information acquisition unit configured to acquire motion information of an imaging device that captures the motion image, wherein the blur correction unit performs the blur correction on the current frame on the basis of the motion information.

(17)

An image processing method for an image processing device configured to correct, frame by frame, a motion image having a predetermined frame rate, the image processing method including, by the image processing device:

an object region detecting step of detecting a region in which a predetermined object that possibly exists on a current frame is photographed;

a blur correction step of performing a blur correction on the current frame; and a replacement step of replacing a pixel value of the region of the object in the frame that has undergone the blur correction using a pixel value of a corresponding region of a frame that has undergone the blur correction and precedes the frame that has undergone the blur correction.

(18)

A program that causes a computer configured to correct, frame by frame, a motion image having a predetermined frame rate to function as:

an object region detecting unit configured to detect a region in which a predetermined object that possibly exists on a current frame is photographed;

a blur correction unit configured to perform a blur correction on the current frame; and a replacement unit configured to replace a pixel value of the region of the object in the frame that has undergone the blur correction using a pixel value of a corresponding region of a frame that has undergone the blur correction and precedes the frame that has undergone the blur correction.

(19)

An endoscope system having an endoscope and an image processing device, wherein the endoscope captures a motion image having a predetermined frame rate and supplies the motion image to the image processing device frame by frame, with the endoscope held inside a tubular retractor so as to have a degree of freedom, and the image processing device includes:

a blur correction unit configured to perform a blur correction on the current frame; and a replacement unit configured to replace a pixel value of the region of the object in the frame that has undergone the blur correction using a pixel value of a corresponding region of a frame that has undergone the blur correction and precedes the frame that has undergone the blur correction.

REFERENCE SIGNS LIST

10 Retractor
11 Endoscope
12 Holding part
20 Marker
21 Marker edge
41 Imaging unit
42 Position sensor
50 Endoscope system
51 Image processing device
52 Image display device
61 Forceps region detecting unit
62 Forceps region holding unit
63 Marker edge detecting unit
64 Center estimation unit
65 Position sensor information acquisition unit
66 Tracking processing unit
67 Marker information holding unit
68 Blur correction unit
69 G image holding unit
70 Replacement unit
100 Computer
101 CPU

The invention claimed is:

1. An image processing device configured to correct, frame by frame, a motion image having a predetermined frame rate, the image processing device comprising processing circuitry configured to:
   detect a marker provided on an operation tool and photographed in a current frame;
   calculate a blur correction amount on the basis of a position of the detected marker; and
   perform a blur correction on the current frame in accordance with the blur correction amount.

2. The image processing device according to claim 1, wherein
   the motion image is captured by an imaging device held inside a tubular retractor so as to have a degree of freedom, and
   the marker is provided on an inner wall of the retractor serving as the operation tool.

3. The image processing device according to claim 2, wherein
   the marker is provided on an end side of the inner wall of the retractor so as to have a zonal shape.

4. The image processing device according to claim 2, wherein
   the imaging device is an endoscope.

5. The image processing device according to claim 2, wherein the processing circuitry is further configured to
   detect a motion vector between a frame that precedes the current frame and has undergone the blur correction and the current frame,
   calculate the blur correction amount on the basis of the position of the detected marker, and
   adjust the calculated blur correction amount using the detected motion vector.

6. The image processing device according to claim 5, wherein the processing circuitry is further configured to
   detect the motion vector by means of pixel matching between the frame that precedes the current frame and has undergone the blur correction and the current frame.

7. The image processing device according to claim 6, wherein the processing circuitry is further configured to acquire motion information of the imaging device, and
   limit a search range of the pixel matching using the acquired motion information.

8. The image processing device according to claim 2, wherein the processing circuitry is further
   configured to detect a region in which a predetermined object that possibly exists on the current frame is photographed, and
   replace a pixel value of the region of the object in the current frame that has undergone the blur correction using a pixel value of a corresponding region of a frame that precedes the current frame and has undergone the blur correction.

9. An image processing method for an image processing device configured to correct, frame by frame, a motion image having a predetermined frame rate, the image processing method comprising, by the image processing device:
   detecting a marker provided on an operation tool and photographed in a current frame;
   calculating a blur correction amount on the basis of a position of the detected marker; and
   performing a blur correction on the current frame in accordance with the blur correction amount.

10. A non-transitory computer readable medium storing computer-readable instructions therein which when executed by a computer cause the computer to perform a method to correct, frame by frame, a motion image having a predetermined rate, the method comprising:
    detecting a marker provided on an operation tool and photographed in a current frame;
    calculating a blur correction amount on the basis of a position of the detected marker; and
    performing a blur correction on the current frame in accordance with the blur correction amount.

11. An endoscope system having an endoscope and an image processing device, comprising:
    the endoscope configured to capture a motion image having a predetermined frame rate and to supply the motion image to the image processing device frame by frame, with the endoscope held inside a tubular retractor so as to have a degree of freedom, and
    the image processing device comprising processing circuitry configured to
    detect a marker provided on an inner wall of the retractor and photographed in a current frame;
    calculate a blur correction amount on the basis of a position of the detected marker; and
    perform a blur correction on the current frame in accordance with the blur correction amount.

* * * * *